United States Patent [19]

Matsumoto et al.

[11] Patent Number: 4,486,549
[45] Date of Patent: Dec. 4, 1984

[54] PROCESS FOR PREPARING AN AMINO GROUP-CONTAINING POLYACRYLONITRILE POLYMER

[75] Inventors: Kunio Matsumoto, Mishima; Rokuro Izumi, Shizuoka; Hideji Seijo, Shizuoka; Hiroyuki Mizuguchi, Shizuoka, all of Japan

[73] Assignee: Toyo Jozo Company, Ltd., Shizuoka, Japan

[21] Appl. No.: 505,376

[22] Filed: Jun. 16, 1983

Related U.S. Application Data

[60] Continuation-in-part of Ser. No. 103,731, Dec. 14, 1979, abandoned, which is a division of Ser. No. 10,997, Feb. 9, 1979, abandoned.

[30] Foreign Application Priority Data

Feb. 17, 1978 [JP] Japan .................. 53-18001

[51] Int. Cl.$^3$ .................. C08J 9/36
[52] U.S. Cl. .................. 521/53; 435/180; 521/134; 521/139; 521/140
[58] Field of Search .................. 521/53; 435/180

[56] References Cited

FOREIGN PATENT DOCUMENTS 1226303 10/1966 Fed. Rep. of Germany .
2084750 12/1971 France .
2228785 12/1974 France .

OTHER PUBLICATIONS

"Reduction of Polymers Using Complex Metal Hydrides", by Cohen et al., J. Org. Chem. 24, 1404–1407 (1959).

Primary Examiner—Morton Foelak
Attorney, Agent, or Firm—Antonelli, Terry & Wands

[57] ABSTRACT

Acrylonitrile polymer containing amino groups and having a porous structure containing micro-pores with an average size of from 50 to 2000 Å and pore volume of not less than 0.2 cm$^3$/g is prepared by reducing an acrylonitrile polymer having said porous structure in an inert non-solvent for said polymer with lithium aluminum hydride. The polymer obtained is useful as a carrier for enzymes.

14 Claims, 1 Drawing Figure

PROCESS FOR PREPARING AN AMINO GROUP-CONTAINING POLYACRYLONITRILE POLYMER

This application is a continuation-in-part of our prior U.S. application Ser. No. 103,731, filed Dec. 14, 1979, now abandoned, which is a divisional of U.S. application Ser. No. 10,997, filed Feb. 9, 1979, now abandoned.

This invention relates to a process for preparation of a carrier comprising a water-insoluble acrylonitrile polymer containing amino groups.

In the prior art, polyacrylonitrile having nitrile groups has been known to have a capacity of adsorbing an enzyme which is a biologically active substance (Japanese published unexamined patent applications No. 121592/1976 and No. 7485/1977). But the amount of the enzyme adsorbed on polyacrylonitrile is small and the adsorbed enzyme will readily be released from the carrier. For this reason, polyacrylonitrile failed to be a good carrier for enzymes. Auslegeschrift No. 1,226,303 discloses polyacrylonitrile having 0.9% of amino group by treating polyacrylonitrile in tetrahydrofuran at 60° C. for 2 hours in the presence of $LiAlH_4$. However, the polyacrylonitrile has a non-porous structure. The non-porous polyacrylonitrile has poor binding ability of biologically active protein; e.g., enzyme, that is, almost no binding occurs for non-porous one.

The present inventors have found that a polyacrylonitrile containing amino groups which is obtained by partial reduction of nitrile groups contained in a porous polyacrylonitrile in solid phase has unexpectedly a high adsorption capacity of enzymes, namely about 2 to 30 times as much as that of the polyacrylonitrile before treatment. The enzymes thus adsorbed on the treated polyacrylonitrile are also found to be difficultly released from the carrier. Furthermore, when an enzyme, which is a biologically active protein, is bonded to the carrier not only through physical adsorption but also when the bonding is strengthened as desired by use of a condensing agent or a crosslinking agent, such a biologically active protein is immobilized with remarkable firmness onto the carrier without suffering from deactivation or deterioration. The resultant immobilized material wherein a biologically active protein is bound to the carrier is found to be active on a substrate, for which said biologically active protein shows specific activity depending on the characteristic thereof, with a long term stability and with good efficiency.

The present invention has been accomplished based on such discoveries as mentioned above, and its object is to provide an immobilized material comprising a carrier having a remarkably large amount of a biologically active protein bound thereto with good stability, a process for producing the same, its use for specific devices and methods as well as a process for producing the carrier for said immobilized material.

In the accompanying drawing:

A graph indicates relationship between the pore diameter and the pore volume of polyacrylonitrile fibers that were prepared at different conditions of spinning.

The specific feature of the present invention resides in using a specific carrier for immobilizing biologically active proteins, which is a water-insoluble acrylonitrile polymer containing amino groups.

The term "acrylonitrile polymer" herein mentioned refers to a polymer of acrylonitrile monomers such as acrylonitrile, methacrylonitrile, α-chloroacrylonitrile, cinnamnitrile, etc. or a copolymer of such monomers with other comonomers containing ethylenically unsaturated double bonds. Typical examples of such comonomers may include styrene monomers such as styrene, methyl-styrene, ethyl-styrene, nitro-styrene, chloro-styrene, bromo-styrene, chloromethyl-styrene and the like; acrylic or methacrylic acid ester monomers such as methyl (meth)acrylate, ethyl (meth)acrylate, butyl (meth)acrylate, 2-hydroxyethyl (meth)acrylate, polyethyleneglycol (meth)acrylate and the like; conjugated dienes such as butadiene, isoprene and the like; halogenated olefins such as vinyl chloride, vinylidene chloride and the like; vinyl ether monomers such as ethyl vinyl ether, butyl vinyl ether and the like; vinyl ketone monomers such as methyl vinyl ketone, ethyl isopropenyl ketone and the like; vinyl ester monomers such as vinyl acetate, vinyl benzoate and the like; amide vinyl monomers such as (meth)acrylamide, N,N-dimethyl(meth)acrylamide, N-vinyl pyrrolidone, N-vinyl succinimide, N-vinyl phthalimide and the like; basic monomers such as vinyl pyridine, methyl vinyl pyridine, vinyl imidazole, N,N-diethylaminoethyl (meth)acrylate and the like; polyfunctional monomers such as divinyl benzene, divinyl toluene and the like; and others. These comonomers may be copolymerized with the acrylonitrile monomers, optionally in the presence of a crosslinking agent such as divinyl benzene, divinyl toluene, etc.

In preparation of the aforesaid carrier, the acrylonitrile polymer is desired to be porous in nature in order to impart good characteristics thereto. For the purpose of obtaining a porous structure, for example, acrylonitrile together with other monomers, if desired, may be subjected to suspension polymerization or emulsion polymerization in an aqueous system. Alternatively, said polymer is dissolved in a soluble solvent such as dimethylformamide, dimethylsulfoxide, conc. nitric acid, an aqueous rhodanate solution, an aqueous zinc chloride solution, etc. and then resultant solution is added dropwise or extruded in the shape of filaments or membranes into a coagulation bath containing water, an aqueous acetone solution, an aqueous ethanol solution, an aqueous dimethylformamide solution, etc. to be formed into particles, fibers or membranes. Furthermore, it is also possible to form the polymer in the shape of hollow filaments. The thus obtained porous structure is presumably considered to have macro-voids which permit biologically active proteins to permeate into inner portions thereof and micro-pores which trap biologically active proteins on the surface or in inner portions thereof. Through such micro-pores, the biologically active proteins are considered to be attached to the carrier. These micro-pores have sizes distributed generally in the range from about 50 to 2000 Å, preferably about 100 to 1000 Å, and pore volume of not less than 0.2 $cm^3/g$.

As the next step, free amino groups are introduced into the acrylonitrile polymer as described above to give the acrylonitrile polymer containing amino groups, namely the carrier according to the present invention. Since immobilization of biologically active proteins is conducted in an aqueous medium, introduction of amino groups should be effected so as to give a water-insoluble carrier. As such methods, there may be employed various reactions well known in the art. For example, nitrile groups in the acrylonitrile polymer may be reduced to be converted to amino groups. When said polymer is previously endowed with porous structure, such reduction may preferably conducted in an inert nonsolvent which does not dissolve said polymer in order to avoid disintegration of the porous structure. As preferable reducing agent for such reduction reactions, there may be employed, for example, lithium aluminum hydride. Since the above reduction reaction is carried out in solid phase, the acrylonitrile polymer employed is desired to be previously endowed with porous structure. As an inert non-solvent, there may be used organic solvents such as diethyl ether, dioxane, tetrahydrofuran, etc. The above reaction may be conducted at room temperature or at around boiling point of the non-solvent employed. The reaction time, which may vary depending on the polymer employed, its shape, its structure or its polymerization degree, may suitably within 10 minutes to 48 hours. As the result of the above reaction, nitrile groups in said polymer are partially converted by reduction to amino groups. The reduction reaction is continued until the carrier is aminated to an extent having at least 20 $\mu$M of amino groups per gram of the carrier but before said carrier is substantailly soluble in water. Usually, the aminated carrier contains 20 to 1000 $\mu$M of amino groups per gram of carrier. It seems that the amino groups are more dense on the surface of the polymer than in the inner portion thereof. The thus obtained carrier may be subjected, if desired, to washing with water, with an acidic aqueous solution or with an alkaline aqueous solution.

As another method for reducing nitrile groups to amino groups, there may also be employed catalytic reduction of an acrylonitrile polymer in an autoclave in the presence of an organic solvent which can dissolve said polymer. But, according to this reaction, amination may proceed to such an extent as rendering the product soluble in water. Furthermore, this method required the step for making the polymer porous. For these reasons, this method is not an advantageous one.

According to still another method for obtaining an acrylonitrile polymer having amino groups, ammonia is allowed to react with an acrylonitrile polymer having halogenic atomic groups, especially chlorine atom groups, to substitute chlorine atom groups with free amino groups. Alternatively, an acrylonitrile polymer containing epoxy groups may be reacted with lysine, an alkylene diamine such as hexamethylene diamine, dodecamethylene diamine, etc. Said polymer can also be obtained by subjecting a copolymer of an acrylonitrile monomer with an amide type vinyl monomer, namely an acrylonitrile polymer having amide groups to Hoffman degradation. Still another method comprises reducing nitro groups of an acrylonitrile polymer containing nitro groups, which is obtained by nitration in conc. nitric acidsulfuric acid mixture of a copolymer of an aromatic vinyl monomer such as styrene monomer, divinyl benzene or vinyl ethyl benzene with an acrylonitrile monomer when said copolymer has no nitro group, with sodium hydrosulfitepotassium hydroxide solution. Furthermore, it is also possible to obtain said polymer by subjecting a copolymer of an acrylonitrile monomer with methyl vinyl ketone to ammonia treatment.

The thus prepared acrylonitrile polymer containing amino groups may be subjected, prior to binding with a biologically active protein if desired, to treatment with a crosslinking agent such as glutaraldehyde in an inert medium such as an aqueous medium preferably with cooling for prevention of polymerization of glutaraldehyde, followed further by treatment with a compound as spacer such as hexamethylene diamine, dodecamethylene diamine or other alkylene diamines, or lysine similarly in an aqueous medium at 0° C. to room temperature, and thereafter subjected again to treatment with a crosslinking agent to give the objective carrier.

The carrier obtained according to the procedure as described above may preferably have a porous structure and is shaped in fibers, particles, membranes or hollow filaments. This porous structure is presumably considered to have macro-voids which permit biologically active proteins to permeate into inner portions thereof and micro-pores which trap biologically active proteins on the surface or in inner portions thereof. The size of the micro-pores are generally from 50 to 2000 Å, more preferably about 100 to 1000 Å.

As the next step, the above carrier which is a porous structure is combined with a biologically active protein, for example, enzymes.

The present invention is further illustrated by the following Examples and Reference examples, by which the present invention is not limited.

In the following Examples and Reference examples, the activity assay when an enzyme is used as biologically active protein is conducted according to the methods as explained below.

Penicillinacylase activity assay (1) Enzyme solution

The reaction mixture comprising 0.5 ml of an enzyme solution, 4.0 ml of 0.1 M phosphate buffer (pH 7.5), and 0.5 ml of 4(W/V)% PcG potassium salt/0.1 M phosphate buffer (pH 7.5) is allowed to react at 37° C. for 30 minutes. A sample (0.5 ml) from the reaction mixture is added to 3 ml of a buffer comprising 1 ml of 0.05 N sodium hydroxide and 2 ml of 20% acetic acid with 0.5 ml of 0.5 (W/V)% P-dimethylaminobenzaldehyde/methanol solution. The resultant mixture is allowed to react at room temperature for 10 minutes. By measurement of absorption at 415 nm, the amount of 6-APA formed is determined.

The enzyme activity which produces 1$\mu$ mole of 6-APA per one minutes is defined as one unit (1 U).

(2) Immobilized enzyme

A previously weighed immobilized enzyme is added to a solution comprising 4.5 ml of 0.1 M phosphate buffer (pH 7.5) and 0.5 ml of 4 (W/V)% PcG potassium salt/0.1 M phosphate buffer (pH 7.5) and the reaction is carried out at 37° C. for 30 minutes. The amount of 6-APA formed is determined similarly as in case of the enzyme solution.

Acylase assay-1

A system comprising 0.25 ml of an acylase containing liquid and 0.25 ml of a solution containing 1% 7-(4-carboxybutaneamido)-desacetoxy cephalosporanic acid as substrate in 0.1 M phosphate buffer (pH 7.0) or a system comprising an immobilized material having acylase bound to a carrier, 2.0 ml of the same substrate solution as mentioned above and 2.0 ml of 0.1 M phosphate buffer is subjected to the reaction at 37° C. for 30 minutes. To 0.5 ml of the reaction mixture containing 7-amino-desacetoxy cephalosporanic acid (7-ADCA) formed after the reaction are added 3 ml of a buffer comprising 1 ml of 0.05 N sodium hydroxide and 2 ml of 2.0% acetic acid and 0.5 ml of a 0.5% p-dimethylaminobenzaldehyde methanol solution. The mixture is allowed to react at room temperature for 10 minutes. The product is subjected to measurement of absorption at 415 nm. The amount of 7-ADCA in sample is calculated from the calibration curve of 7-ADCA. The activity which produces 100 γ/ml of 7-ADCA is defined as 100 U.

This measurement method is conducted by utilizing the acylase produced from Comamonas sp. SY-77-1(FERM-P 2410).

Acylase assay-2

In place of the substrate used in the above acylase assay-1, there is used 0.1 M phosphate buffer (pH 7.5) containing 1% 7-phenylacetamidodesacetoxy cephalosporanic acid under otherwise the same conditions as in the acylase assay-1. In this assay, there is used the acylase produced from *Bacillus megaterium* B-400 (FERM-P 748).

Cholineoxidase activity assay

A system comprising 5 μl of a cholineoxidase containing solution or 1 to 5 mg of an immobilized material having cholineoxidase bound to a carrier, 0.05 ml of 0.2 M tris-hydrochloride buffer (pH 8.0), 0.05 ml of 3 mg/ml 4-aminoantipyrin, 0.10 ml of 0.1% phenol, 0.10 ml of 2 U/mg peroxidase, 0.10 ml of 0.1 M choline chloride and 0.1 ml of distilled water is subjected to the reaction at 37° C. for 5 minutes. The reaction is terminated with addition of 2.5 ml of ethanol. Absorption is measured at 480 nm. The activity which produces 1μ mole of hydrogen peroxide per one minute is defined as 1 U. The activity of said immobilized material is calculated according to the following formula:

$$\text{Activity (U/g)} = \frac{\Delta A480 \text{ nm} \times 0.35 \times 1000}{\text{reaction time (min.)} \times \text{immobilized material (mg)}}$$

In the above assay, there is used choline-oxidase which is produced from *Arthrobacter globiformis* B-0577.

Phospholipase D activity assay

A system comprising 0.05 ml of a phospholipase D containing solution, 0.1 ml of 0.2 M tris-hydrochloride buffer (pH 8.0), 0.1 ml of 10 mM lecithin emulsion, 0.05 ml of 0.1 M calcium chloride, 0.1 ml of 1% Triton X-100 and 0.1 ml of water is subjected to the reaction at 37° C. for 10 minutes. Alternatively, a system comprising 1 to 5 mg of an immobilized material having bound phospholipase D to a carrier, 0.15 ml of 0.2 M tris-hydrochloride buffer (pH 8.0), 0.1 ml of 10 mM lecithin emulsion, 0.05 ml of 0.1 M calcium chloride, 0.1 ml of 1% Triton X-100 and 0.1 ml of water is subjected to the reaction at 37° C. for 5 minutes. The reaction is then terminated by boiling the system, followed by cooling to 37° C. To the reaction mixture are added 0.1 ml of 4-aminoantipyrine (3 mg/ml), 0.1 ml of 2 U/ml peroxidase, 0.10 ml of 0.1% phenol, 0.1 ml of 12 U/ml cholineoxidase and 0.1 ml of water. The resultant mixture is subjected to the reaction at 37° C. for 20 minutes. After addition of 2 ml of 1% Triton X-100 to the reaction mixture, absorption is measured at 500 nm. The activity producing 1μ mole of choline per one minute is determined as 1 U. The activity of said immobilized material is calculated according to the following formula:

$$\text{Activity (U/g)} = \frac{\Delta A500 \text{ nm} \times 0.25 \times 1000}{\text{Reaction time (min.)} \times \text{immobilized material (mg)}}$$

In this method, there is utilized phospholipase D.

The various methods for assay of enzyme activities as described are only examples and other known methods may be used. It is also possible to use other methods suitable for the enzymes utilized. In case when the utilized enzyme is the immobilized enzyme according to the present invention, it can be provided as enzyme electrode with attachment of reaction vessel and measuring means to assemble an device, and in said reaction vessel there may be employed a system comprising a suitable combination of various reagents corresponding to the enzyme utilized and solutions containing corresponding substrate as sample and reference to carry out the measurement according to the methods as described above.

Glucose oxidase

The determination of the activity of glucose oxidase is conducted according to the method similar to that for the determination of choline oxidase except that 0.10 ml of a 1% glucose solution is used instead of 0.1 M choline chloride solution mentioned above.

Lactate oxidase

A system consisting of 20 μl of a solution containing lactate oxidase or 1-5 mg of an immobilized enzyme prepared by binding lactate oxidase to a carrier, 0.2 ml of a 0.2 M dimethylglutaric acid buffer solution (pH 6.5), 0.1 ml of a 3 mg/ml 4-aminoantipyrine solution, 0.1 ml of 0.2%-N,N-dimethylaniline solution, 0.2 ml of a peroxidase solution having an activity of 2 U/mg and 0.3 ml of distilled water is allowed to react at 37° C. for 10 minutes. Then 2 ml of a 0.1% laurylbenzene sulfonic acid solution is added to the resultant product to terminate the reaction and the absorbance of the product at 565 nm is determined. The activity which produces 1 μmole of hydrogen peroxide is defined as 1 U. The enzyme activity of said immobilized enzyme is calculated according to the following equation:

$$\text{Activity (U/g)} = \frac{\Delta 565 \text{ nm}}{10} \times \frac{1}{5.85} \times \frac{1000}{\text{immobilized enzyme (mg)}}$$

EXAMPLE 1

Preparation of polyacrylonitrile having porous structure

A three-necked flask of 500 ml capacity is immersed in a thermostat water-bath maintained at about 35° C. and replaced with nitrogen for about 15 minutes. Then, into the flask is charged 120 ml of distilled water, followed further by addition of 2 g of sodium alkylsulfonate, 80 g of acrylonitrile, 0.1 g of sodium persulfate and 0.033 g of hydrous sodium sulfite. After stirring the mixture for about 3 hours, there is obtained an emulsion. The emulsion is poured into about 500 ml of water and sodium chloride is added thereto to effect precipitation of the product by coagulation. The precipitates are separated by filtration, washed with water and dried on air to give polyacrylonitrile having an inherent viscosity of about 10.5 (as measured in 0.5% dimethylformamide solution at 30° C.).

Then, 10 g of this polyacrylonitrile is dissolved in 150 ml of dimethylformamide and the resultant solution is extruded in the form of filaments into a 20% aqueous dimethylformamide solution to prepare filaments (thickness: 20 to 35 microns) of polyacrylonitrile (containing 90% or more of acrylonitrile) having a porous structure.

The same polyacrylonitrile solution is added dropwise by an atomizer cup into a 20% aqueous dimethylformamide solution, whereby there are obtained particles of of polyacrylonitrile having a porous structure (pore diameter: 100–1000 Å, pore volume: 0.90 cm$^3$/g).

EXAMPLE 2

Preparation of aminated polyacrylonitrile

To 1.5 g of lithium aluminum hydride is added 120 ml of dry diethyl ether. The porous polyacrylonitrile fiber (containing 90% or more of acrylonitrile), 1.5 g obtained in Example 1 is added to the resultant solution. With equipment of a reflux condenser, the mixture is subjected to heating under reflux in an oil bath at 50° C. for 10 minutes to 30 hours. After the reaction, the fibers are taken out, washed with dry diethyl ether, followed by thorough washing with 1 N hydrochloric acid, water, 1 N aqueous sodium hydroxide solution and water, successively, to give aminated polyacrylonitrile fibers (thickness: 20 to 35 microns). The unaltered lithium aluminum hydrochloride is decomposed by dropwise addition of a small quantity of water.

The aminated polyacrylonitrile fibers obtained having the following physical properties:
Color: slightly more colored in yellow than polyacrylonitrile, yellowish color being intensified as the reduction time is prolonged;
Viscosity: unmeasurable because not soluble in the solvents as set forth below;
Solubility in various solvents:

|  | Aminated polyacrylonitrile fibers; | Polyacrylonitrile fibers |
| --- | --- | --- |
| DMSO (dimethylsulfoxide) | partly soluble | soluble |
| DMF (dimethylformamide) | " | " |
| conc. nitric acid | " | " |
| 65% KSCN solution | " | " |
| chloroform | insoluble | insoluble |
| acetonitrile | " | " |
| pyridine | " | " |
| nitromethane | " | " |
| cyclohexane | " | " |
| diethyl ether | " | " |
| dioxane | " | " |
| tetrahydrofuran | " | " |
| 30% aqueous NaOH solution | " | " |

*not completely dissolved, while remaining the thickness of fibers without substantial change; partial solubility is detected by turbidity of the solvent by addition of water as well as from the loss in weight as shown in the following experiment.

Various aminated polyacrylonitrile fibers, each 30 mg, obtained after various reduction time are added into 5 ml of dimethylformamide and each mixture is subjected to heat treatment at 60° C. for 3 minutes. Then, the fibers are separated by filtration, washed with water and dried. The weight of the fibers after drying is measured to give the results as set forth below:

| Reduction time | Loss in weight (%) |
| --- | --- |
| 5 minutes | 31.3 |
| 1 hour | 29.0 |
| 5 hours | 27.0 |

Color indication by sodium 2,4,6-trinitrobenzene sulfonate is not recognized for polyacrylonitrile fibers, but the aminated polyacrylonitrile fibers are found to indicate yellow color, whereby the presence of amino groups can be confirmed.

Content of amino groups

The results of measurement of the immobilized protein and the estimated content of amino groups on the carrier as determined from the following test methods are shown in Tables 1 to 3.

(1) Immobilized enzyme

Various carriers as obtained above after various reaction time, each 18 mg, are added into 10 ml of 12.5% glutaraldehyde/borate buffer (pH 8.5) and each mixture is stirred at 0° C. for 20 minutes. The fibers are separated by filtration and thoroughly washed with borate buffer (pH 8.5) and 0.1 M phosphate buffer (pH 7.5). Immediately thereafter, the fibers are put into 2 ml of 0.3% bovine serum alubumin or penicillinacylase (140 U/ml) of Bacillus megaterium B-400/0.1 M phosphate buffer (pH 7.5), and the mixture is subjected to shaking at 30° C. for one hour. After filtration, bovine serum alubumin or penicillinacylase remained in the mother liquor are quantitatively measured by Lowry method [(O. H. Lowry, J. Biol. Chem., 193, 265(1951)] to determine the content of bovine serum alubumin or penicillinacylase bound onto said carrier.

Said carrier, without treatment with glutaraldehyde, is also directly put into the bovine serum alubumin solution or the penicillinacylase solution, followed by shaking at 30° C. for one hour, determine the amount of bovine serum alubumin or penicillinacylase adsorbed on said carrier according to the procedure as described above.

(2) Estimated content of amino groups by amino acid attachment

Each of various carriers (18 mg) as obtained above after various reaction time is similarly treated in (1) with 12.5% glutaraldehyde solution, and thereafter put into 2 ml of a 0.1 M phosphate buffer (pH 7.5) containing 0.3% each of glutamic acid (Glu), threonine(Thr) or 7-amino desacetoxy cephalosporanic acid (7-ADCA), followed by shaking at 30° C. for one hour. The reaction mixture is separated by filtration and the amino acid content in the supernatant is quantitatively determined by automatic amino acid analyzer, from which the amino acid content in said carrier is determined as the amino acid binding capacity. In practicing this experiment, the absence of adsorption capacity of the amino acids employed on said carrier is confirmed by the experiment in which amino acid hydrazide is used in place of amino acid. When 7-ADCA is employed as the amino acid, the content in the supernatant is determined by means of high speed liquid chromatography from the absorption in the ultraviolet region at 254 nm to determine 7-ADCA binding capacity of the carrier.

(3) Estimated content of amino groups by titration

Each of various carriers obtained after various reduction time (80 mg) is stirred together with 15 ml of a 2 mM hydrochloric acid and 30 ml of distilled water for one hour. The excessive hydrochloric acid is titrated with 2 mM aqueous sodium hydroxide solution to determine the amount of the hydrochloric acid consumed as hydrochloride corresponding to the content of amino groups in the sample carrier.

TABLE 1

| | Amount of bound protein | | | |
|---|---|---|---|---|
| | Bovine serum alubumin γ/mg | | Penicillinacylase γ/mg | |
| Reflux time (hours) | Glutar- aldehyde treatment | Adsorption with no treatment | Glutar- aldehyde treatment | Adsorption with no treatment |
| 0 | 10 | 10 | 13 | 6 |
| 1/6 | 80 | 24 | 145 | 66 |
| 0.5 | 83 | 27 | 160 | 84 |
| 6 | 89 | 42 | 155 | 85 |
| 30 | 74 | 51 | 149 | 97 |

TABLE 2

| | Amino acid attachment capacity | | |
|---|---|---|---|
| Reflux time | Amino acid attachment capacity μM/g | | |
| (hours) | Glu | Thr | 7-ADCA |
| 0 | 0 | 0 | 0 |
| 0.5 | 86 | 51 | 46 |
| 6 | 73 | 120 | 44 |
| 30 | 92 | 84 | 45 |

TABLE 3

| Amount of hydrochloric acid consumed by titration | |
|---|---|
| Reflux time | Content of amino groups μM/g |
| 0 min. | 0 |
| 5 min. | 175 |
| 30 min. | 230 |
| 1 hour | 263 |
| 3 hours | 300 |
| 5 hours | 300 |
| 8 hours | 275 |

Amount of the enzyme (penicillinacylase) adsorbed

In place of determining the amount of penicillinacylase produced from *Bacillus megaterium* B-400 (FERM-P 748) attached on the carrier in the preceding item (1), the activity of penicillinacylase is determined according to the penicillinacylase activity assay as previously described. The results are shown in Table 4.

TABLE 4

| | Specific activity of penicillinacylase | |
|---|---|---|
| Reflux time (hours) | Glutaraldehyde treatment U/mg | Adsorption with no treatment U/mg |
| 0 | 0.12 | 0.10 |
| 1/6 | 2.88 | 3.05 |
| 0.5 | 2.90 | 3.00 |
| 1 | 2.85 | 3.05 |
| 6 | 2.83 | 3.05 |

From the results of Table 1 and Table 3, as the reaction time of hydrogenation increasing, the amount of primary amino groups increased, but the amount of immobilized penicillinacylase activity per gram of dry aminated porous PAN fibers and the amount of immobilized protein increased only within 5 minutes of the reaction and after 5 minutes those values reached to the maximum values, about 145 γ/mg and 80 mg per gram of dry aminated porous PAN fibers respectively. That, a certain extent of primary amino groups is necessary for the immobilization but the immobilized enzyme activity does not depend on the amount of primary amino groups.

EXAMPLE 3

Into a three-necked flask is charged 2.5 g of lithium aluminum hydride and 100 ml of dry diethyl ether is added thereto, followed by stirring the mixture. To the resultant mixture is added 2 g of particles (average particle size: 100 mesh) of the porous acrylonitrile as prepared in Example 1 and the mixture is heated under reflux at 50° C. for 16 hours. After the reaction, to the reaction mixture is added dropwise water under ice-cooling to decompose unaltered lithium aluminum hydride. Further, by dropwise addition of 1N hydrochloric acid, the decomposed product is dissolved. The aminated polyacrylonitrile is recovered by filtration and then washed successively with 1N hydrochloric acid, water, 1N sodium hydroxide, water and 0.1M phosphate buffer (pH 7.5) to give pale yellow polyacrylonitrile particles containing amino groups having a porous structure (average particle diameter: 100 mesh).

EXAMPLE 4

A mixture of 2 g of lithium aluminum hydride with 50 ml of dry diethyl ether is stirred and to the mixture is added under cooling little by little 3 g of particles (average diameter: 100 mesh) of an acrylonitrile type copolymer having a porous structure comprising 55 parts of acrylonitrile, 25 parts of divinyl benzene and 20 parts of vinyl ethyl benzene prepared similarly as described in Example 1. The resultant mixture is heated under reflux at 45° C. for 10 minutes to 8 hours and then 2 ml of water is added to the reaction mixture with stirring under cooling in an ice-bath to decompose unaltered lithium aluminum hydride. Further, after addition of 1N hydrochloric acid to the mixture, the insoluble polymer containing amino groups is separated by filtration and washed to give particles (average size: 100 mesh; wet weight=9 g) of an aminated polyacrylonitrile copolymer having a porous structure.

The thus prepared aminated copolymer has the following physical and chemical properties:

Color: pale yellow, yellowish color being intensified as the reduction time is prolonged;

Viscosity: not measurable due to insolubility in the solvents as set forth below;

Solubility in solvents: insluble in DMSO, DMF, conc. nitric acid, 65% KSCN solution (60° C.), chloroform, acetonitrile, pyridine, nitromethane, cyclohexane, diethyl ether, and 30% aqueous sodium hydroxide solution;

Content of amino groups: estimated content of amino groups as measured by the hydrochloric acid titration method as described in Example 2 are as follows:

| Reduction time | Content of amino groups (amount of hydrochloric acid consumed) |
|---|---|
| 10 minutes | 545 μM/g-carrier |
| 1 hour | 738 |

| Reduction time | Content of amino groups (amount of hydrochloric acid consumed) |
| --- | --- |
| 8 hours | 780 |

The particles of the polyacrylonitrile copolymer having porous structure of the starting material (Control) and the particles of the aminated polyacrylonitrile copolymer having porous structure (present invention) have capacities for attaching various enzymes as set forth in the following Table:

| Enzyme | Present invention | Control |
| --- | --- | --- |
| Acylase produced from *Bacillus megaterium* B-400 | 150 U/mg | 40 U/mg |
| Acylase produced from *Comamonas* sp. SY-77-1 | 670 U/mg | 350 U/mg |
| Cholineoxidase produced from *Arthrobacter globiformis* B-0577 | 7.0 U/mg | 0.45 U/mg |

The above capacities are measured by the following method. Namely, 50 to 100 mg of the sample of the polymer according to the present invention or Control is put into an L-shaped test tube and a buffer containing each enzyme is added thereto. After stirring the mixture at 30° C. for 60 minutes, the reaction mixture is separated by filtration and washed with 0.5N sodium chloride/0.1M phosphate buffer (pH 7.5), followed by washing with 0.1M phosphate buffer (pH 7.5). The product obtained is then subjected to the activity assay as described above.

EXAMPLE 5

After washing 9 g of particles of the aminated polyacrylonitrile copolymer having a porous structure as prepared in Example 4 with 0.1M phosphate buffer (pH 7.5), the washed particles are put into 200 ml of a previously cooled 12.5% glutaraldehyde/phosphate buffer (pH 8.5), followed by stirring at 0° C. for 20 minutes. This carrier is collected by filtration, sufficiently washed with 0.1M phosphate buffer (pH 7.5) and put into 60 ml of a solution of the acylase enzyme (60 U/ml) produced from *Bacillus megaterium* B-400. After stirring the mixture at 4° C. overnight, the carrier is separated by filtration and washed with 0.5M sodium chloride/0.1M phosphate buffer (pH 7.5), and then with 0.1M phosphate buffer (pH 7.5), to give 8.7 g immobilized material having bound said particles with the acylase (acylase activity 324 U/g).

EXAMPLE 6

A mixture of 3.8 g of lithium aluminum hydride with 120 ml of dry diethyl ether is mixed with 2.5 g of polyacrylonitrile fibers (acrylonitrile 95%; thickness 20 to 35 microns). The reduction reaction is carried out at 45° C. for 24 hours under stirring. Then, with stirring under cooling in an ice-bath, 3 ml of water is added dropwise to the reaction mixture. Further, 1N HCl is added little by little to the mixture until generation of hydrogen gas is stopped, whereupon the product is separated by filtration to give 12.5 g (wet weight) of aminated polyacrylonitrile fibers having a porous structure.

As the next step, 600 mg (wet weight) of the fibers as prepared above are washed with 0.1M phosphate buffer (pH 7.5) and put into 50 ml of a cooled 12.5% glutaraldehyde/phosphate buffer (pH 8.5), followed by stirring at 0° C. for 20 minutes. The treated fibers are separated by filtration and then washed with 0.1M phosphate buffer (pH 7.5). The resultant carrier is put in 8 ml of an acylase solution (108,000 U/ml) produced from *Comamonas* sp. SY-77-1 and the mixture is stirred at room temperature for 5 minutes. After addition of 10 μl of 25% glutaraldehyde, the mixture is further stirred at 30° C. for 60 minutes. Then, the product is separated by filtration to recover solid components, which are washed with 0.5M sodium chloride/0.1M phosphate buffer (pH 7.5) and then with 0.1M phosphate buffer (pH 7.5) to obtain 300 mg (wet weight) of immobilized enzyme having bound acylase to the said fibrous carrier (acylase activity 1600 U/mg).

Subsequently, 4.5 g (wet weight) of the thus prepared immobilized enzyme is packed in a jacketed column (1×5 cm, V=4 ml) and washed with 0.1M phosphate buffer (pH 7.5). Into the column is continuously charged at space velocity of 1.5 a solution of 9.92 mg/ml of 7-(4-carboxybutaneamido)-cephalosporanic acid in 0.1M phosphate buffer. The effluent containing 7-amino-cephalosporanic acid (7-ACA) is subjected to measurement by PDAB method and its content is determined from the calibration curve of 7-ACA. The curve is prepared on the basis of an amount of liquor passed on abscissa versus percentage of cleavage which is the yield of 7-ACA on ordinate. It can clearly been seen that the immobilized enzyme of the present invention can be used favorably for a long time without deterioration in enzyme activity. Furthermore, 600 ml of the effluent containing 7-ACA as mentioned above (percentage of cleavage=84.5%) is adjusted to pH 3.2, concentrated to about 55 ml and left to stand at 4° C. overnight, whereby 3.22 g of 7-ACA precipitates (purity=86.3%) are obtained.

EXAMPLE 7

The aminated acrylonitrile fibers as prepared in Example 6 (0.6 g, wet weight) are put into 50 ml of an ice-cooled 12.5% glutaraldehyde/borate buffer (pH 8.5) and the mixture is stirred at 0° C. for 20 minutes. Then, said fibers are separated by filtration and washed with borate buffer (pH 8.5) and then with 0.1M phosphate buffer (pH 7.5). The treated fibers are mixed with 12 ml of a 0.1M phosphate buffer solution (pH 7.5) containing 20 U/ml of phospholipase D and 5 U/ml of cholineoxidase, and the mixture is stirred at 0° C. overnight. The product is separated by filtration and washed with 0.5M sodium chloride/0.1M phosphate buffer (pH 7.5) to give immobilized enzyme having phospholipase D and cholineoxidase bound to said fibrous carrier (phospholipase D activity: 119 U/g, cholineoxidase activity; 17 U/g).

EXAMPLE 8

The polyacrylonitrile as obtained in Example 1 is similarly dissolved in dimethylformamide and a membrane is formed from the resultant solution in a water-bath containing 15% dimethylformamide. The membrane is washed with water and dried in air to give an polyacrylonitrile membrane. This membrane (450 mg) is heated under reflux in the presence of 700 mg of lithium aluminum hydride and 30 ml of diethyl ether for 18 hours to give 520 mg (wet weight) of an aminated polyacrylonitrile membrane having a porous structure. Then, 150 mg of this membrane is mixed with 40 ml of 12.5% glutaraldehyde/borate buffer (pH 8.5) and the mixture is stirred at 0° C. for 20 minutes. The treated membrane is separated by filtration and mixed with stirring at 30° C. for 60 minutes with 5 ml of a 0.1M phosphate buffer (pH 7.5) containing 15 mg of cholineoxidase (3.6 U/mg). The product is separated by filtration and washed with 0.5M sodium chloride/0.1M phosphate buffer (pH 7.5), and then with 0.1M phosphate buffer (pH 7.5), to give an immobilized enzyme having cholineoxidase bound to said membrane (cholineoxidase activity 3 U/g).

EXAMPLE 9

The same aminated polyacrylonitrile membrane as used in Example 8 (10 mg; wet weight) is mixed with stirring at 0° C. for 20 minutes with 40 ml of a 12.5% glutaraldehyde/borate buffer (pH 8.5). After filtration and washing with 0.1M phosphate buffer (pH 7.5), the treated membrane is mixed with stirring at 30° C. for 60 minutes with 5 ml of 0.1M phosphate buffer (pH 7.5) containing 10 mg of glucoseoxidase (produced by Behlinger Co.) (210 U/mg). Then, the product is separated by filtration and washed with 0.5M sodium chloride/0.1M phosphate buffer (pH 7.5) and further with 0.1M phosphate buffer (pH 7.5) to give an immobilized enzyme (glucoseoxidase activity 150 U/g) having glucoseoxidase bound to said membrane.

EXAMPLE 10

A solution of 160 mg (3.6 U/mg) of cholineoxidase dissolved in 5 ml of 0.1M phosphate buffer (pH 7.5) is mixed with stirring in an ice-bath with 100 mg (wet weight) of the aminated polyacrylonitrile fibers as obtained in Example 6. To this mixture is added 20 μl of 1-ethyl-3-(3-dimethylaminopropyl)-carbodiimide and the mixture is adjusted with 1N HCl to pH 7.5. The mixture is stirred in an ice-bath for 3 hours and further at 4° C. overnight. The product is separated by filtration and washed with 0.5M sodium chloride/0.1M phosphate buffer (pH 7.5) and then with 0.1M phosphate buffer (pH 7.5) to give immobilized enzyme having cholineoxidase bound to said fibrous carrier (cholineoxidase activity: 5.6 U/mg).

EXAMPLE 11

Example 10 is repeated except that 5 ml of acylase solution (96 U/ml) produced from *Bacillus megaterium* B-400 in place of cholineoxidase and 40 μl of 1-ethyl-3-(3-dimethylaminopropyl) carbodiimide are used, whereby there is obtained an immobilized enzyme having acylase bound to said fibrous carrier (acylase activity: 264 U/g).

EXAMPLE 12

The particles of the aminated polyacrylonitrile copolymer as obtained in Example 4 (500 mg; wet weight) are mixed with stirring at 0° C. for 20 minutes with 30 ml of 12.5% glutaraldehyde/borate buffer (pH 8.5). The treated particles are separated by filtration and thoroughly washed with 0.1M phosphate buffer (pH 7.5). The particles are then mixed with stirring at 4° C. for 24 hours with 30 ml of 0.5M aqueous hexamethylene diamine solution (pH 9.5), followed by filtration and thorough washing with water. Further, the product is treated with 12.5% glutaraldehyde/borate buffer (pH 8.5), followed by washing with water, and mixed with stirring at 4° C. for 12 hours with 5 ml of an acylase solution (72 U/ml) produced from *Bacillus megaterium* B-400 (FERM-P 748). After filtration and washing with 0.5M sodium chloride/0.1M phosphate buffer (pH 7.5), and then with 0.1M phosphate buffer (pH 7.5), there is obtained 440 mg (wet weight) of an immobilized enzyme having acylase bound to said particulate carrier (acylase activity: 250 U/g).

EXAMPLE 13

In a jar fermenter of 30-liter capacity are charged 20 liters of a medium (pH 6.0) comprising 2% glucose, 0.4% potassium hydrogen phosphate, 0.1% magnesium sulfate, 0.05% potassium chloride, 0.0025% ferrous sulfate, 0.1% yeast extract and 0.3% DL-methionine. After sterilization at 120° C. for 20 minutes, *Trigonopsis variabilis* CBS 4095 is inoculated to the medium and cultivation is carried out at 30° C. for 48 hours to obtain about 20 liters of culture broth. The culture broth is subjected to filtration to obtain about 400 g of microorganism cells. The microorganism cells are then dispersed in 800 ml of 0.1M phosphate buffer (pH 7.5) and sufficiently crushed with addition of 1000 g of glass beads (diameter: 0.25 to 0.30 mm). The mixture is subjected to centrifugation under cooling at 15,000 r.p.m. for 20 minutes and the resultant supernatant (D-amino acid oxidase activity 15,000 U/ml), 1000 ml, is treated with Carbowax (average molecular weight=about 20,000) to obtain 100 ml of concentrated solution of D-amino acid oxidase (145,000 U/ml).

To the thus prepared concentrated solution (10 ml) in an L-shaped test tube is added one gram of the polyacrylonitrile (acrylonitrile: 95%) fiber having a porous structure (as Control) or the aminated polyacrylonitrile (acrylonitrile: 95%) fiber as prepared in Example 6 (as Present invention). Each mixture is stirred at 30° C. for 60 minutes. The product is separated by filtration and washed with water. The enzyme attached on each fibrous carrier is assayed for its activity to give the result of D-amino acid oxidase activity for the fibrous carrier of Controls of 7.5 U/mg (attachment percentage: 0.5%) and that for the fibrous material of the present invention of 276 U/mg (attachment percentage: 19.0%), the latter being by far superior to the former.

The activity of said D-amino acid oxidase is conducted by the following method. That is, a system comprising 0.5 ml of the enzyme solution and 1.0 ml of 0.1M phosphate buffer (pH 7.5) (or immobilized enzyme of the present invention and 1.5 ml of 0.1M phosphate buffer of pH 7.5), 0.5 ml of an indicator (prepared by dissolving 5 mg 0-dianisidine in one ml of ethanol, adding 0.3 ml of the resultant solution to 10 ml of 0.1M phosphate buffer and further adding 2 mg of peroxidase 8 U/mg thereto) and 0.5 ml of 2% aqueous alanine solution is allowed to react at 37° C. for 15 minutes. The reaction is terminated by adding 0.5 ml of 50% trichloro acetic acid to the reaction mixture and 2.0 ml of ethanol is further added thereto, followed by centrifugation at 10,000 r.p.m. for 5 minutes. The supernatant is recovered and subjected to measurement of absorption at 400 nm. The enzyme activity which changes the absorption by 0.100 after the reaction time of 15 minutes is determined as 100 U.

EXAMPLE 14

A mixture of 1.5 g of polyacrylonitrile fibers (acrylonitrile: 90% or more) having a porous structure with 120 ml of dry diethyl ether containing 1.5 g of lithium aluminum hydride is heated under reflux in an oil-bath at 50° C. for 21 hours. Then, the reduced product is separated by filtration and washed successively with ether, a small amount of water, 1N HCl, water, 1N NaOH, water and 0.1M phosphate buffer (pH 7.5) to prepare an aminated polyacrylonitrile fiber (7 g as wet weight) having a porous structure.

Then, the fibers are put into 240 ml of a cooled 12.5% glutaraldehyde/borate buffer (pH 8.5) and the mixture is stirred at 0° C. for 20 minutes. The treated fibers are separated by filtration, washed with borate buffer (pH 8.5) and then with 0.1M phosphate buffer (pH 7.5). The resultant fibers and 113 ml of an acylase solution (60 U/ml) produced from *Bacillus megaterium* B-400 (FERM-P 748) are mixed with stirring at room temperature for 4 hours and left to stand at 5° C. overnight. The product is separated by filtration (no acylase activity being recognized in the filtrate). The product is further washed with 0.5M sodium chloride/0.1M phosphate buffer (pH 7.5) and 0.1M phosphate buffer (pH 7.5) to give 6.8 g (wet weight) of immobilized enzyme having the acylase bound to said fibrous carrier (584 U/g).

EXAMPLE 15

Particles (2 g of an acrylonitrile copolymer; about 100 μ in diameter) comprising 55 parts of acrylonitrile, 25 parts of divinyl benzene and 20 parts of vinyl ethyl benzene having a porous structure are subjected to nitration in 47% nitric acid-sulfuric acid mixture at 0° C. for 60 minutes. After washing with water, the product is reduced in a 6% sodium hydrosulfite/2N aqueous KOH solution at 60° C. for 2 hours. The resultant product is thoroughly washed with water to give 5.5 g (wet weight) of aminated polyacrylonitrile copolymer having a porous structure.

The thus prepared particles (90 mg as wet weight) are stirred in a 12.5% glutaraldehyde/borate buffer (pH 8.5) at 0° C. for 20 minutes, followed by washing with 0.1M phosphate buffer (pH 7.5). Then, the treated particles are mixed with 3 ml of an acylase solution (84 U/ml) produced from *Bacillus megaterium* B-400 (FERM-P 748) with stirring at 30° C. for 60 minutes. The product is collected by filtration and washed with 0.05M sodium chloride/0.1M phosphate buffer (pH 7.5) and with 0.1M phosphate buffer (pH 7.5) to prepare an immobilized enzyme (118 U/g) having the acylase bound to said particulate carrier. This product can be used in the various devices as explained in the foregoing.

EXAMPLES 16 TO 18

(a) A three-necked flask of 500 ml capacity is equipped with a pipe for introducing nitrogen, a stirrer and a reflux condenser. The flask is dipped in a thermostat water-bath maintained at about 40° C. and replaced with nitrogen for 15 minutes. Then, into this flask is charged 120 ml of distilled water having 1 g of sodium alkyl sulfonate dissolved therein. While stirring the solution, 70 g of acrylonitrile and 10 g of styrene free from inhibitors are added thereto to be emulsified, followed by addition of 0.1 g of potassium persulfate. The polymerization is conducted for 20 to 22 hours to prepare emulsions containing particles of 0.1 to 1.0 μ in diameter. The resultant emulsion is poured into 500 ml of water and coagulated with sodium chloride under stirring. The product of acrylonitrile-styrene copolymer is filtered, washed with water and dried, followed by removal of unaltered monomers under reduced pressure. The copolymer has an intrisic viscosity of 1.3 in dimethylformamide. This copolymer (10 g) is dissolved in 200 ml of dimethylformamide and the solution is added dropwise by an atomizer cup into 50 liters of a 20% aqueous acetone solution to prepare hydrate particles having a porous structure (size: 0.5 to 1 mm).

(b) Using the same apparatus as described in (a), a mixture of 300 ml of distilled water containing 2 g of Triton 720 (produced by Rohm & Haas Co., U.S.A.) and 2 g of Tergitol (produced by Union Carbide Co., U.S.A.) therein with 0.2 g of potassium persulfate is stirred and 80 g of acrylonitrile, from which inhibitors are previously removed, and 20 g of distilled methyl acrylate are added thereto. Polymerization is conducted by heating at 40 to 50° C. After 30 minutes, polymerization is carried out at reflux temperature of 90° C. After the reaction, the resultant suspension is subjected to steam distillation for 15 to 20 minutes to remove unaltered monomers. Then, after the product is salted out similarly as in (a) and dried on air, there is obtained an acrylonitrile-methyl acrylate copolymer having an intrinsic viscosity of 1.2 in dimethylformamide. This copolymer (10 g) is dissolved in 100 ml of dimethylsulfoxide and the solution is added dropwise by an atomizer cup into a 20% aqueous dimethylsulfoxide solution to prepare particles (0.5 to 1 mm in diameter) of said copolymer in the form of hydrated gels having a porous structure.

(c) The procedure as described in (a) is repeated except that 10 g of divinyl benzene is used in place of styrene to prepare particles (0.5 to 1 mm in diameter) of acrylonitrile-divinyl benzene copolymer in the form of hydrated gels having a porous structure.

Using each 2 g of the particles of the copolymers having porous structure as obtained in the above (a), (b) and (c), the following reduction reaction is carried out. Namely, 2.5 g of lithium aluminum hydride is added into a three-necked flask and stirred with 100 ml of dry diethyl ether. To the mixture is added 2 g of each copolymer and the reaction is conducted under heating with reflux at constant temperature at 50° C. for 16 hours. After the reaction, the product is treated with water and 1N HCl in an ice-bath, followed by successive washing with 1N HCl, water, 1N NaOH, water and 0.1M phosphate buffer (pH 7.5), to prepare particles having a porous structure containing free amino groups and nitrile groups.

Each of the above particles having porous structure containing free amino groups and nitrile groups (300 mg as wet weight) is treated with 50 ml of an ice-cooled 12.5% glutaraldehyde/borate buffer (pH 8.5) with stirring at 0° C. for 20 minutes. The treated fibers are collected by filtration and washed with 0.1M phosphate buffer (pH 7.5). Then, the particles are put into 3 ml of an acylase solution (72 U/ml) produced from Bacillus megaterium B-400 (FERM-P 478) in an L-shaped test tube and the mixture is stirred at 30° C. for 60 minutes. The product is filtered, washed with 0.5M sodium chloride/0.1M phosphate buffer (pH 7.5) and then with 0.1M phosphate buffer (pH 7.5) to give objective immobilized enzymes having acylase bound to the particulate carriers, respectively.

Furthermore, using the particles of the aminated polyacrylonitrile having a porous structure prepared in Example 3, acylase is found similarly as described above thereto to prepare an immobilized enzyme.

As the result, the acylase activity in the immobilized enzyme using the copolymer as obtained in (a) is found to be 162 U/g; that in (b) 216 U/g; that in (c) 192 U/g;

and that, using the aminated polyacrylonitrile obtained in Example 3, 252 U/g, respectively.

EXAMPLE 19

The particles of the aminated polyacrylonitrile having porous structure obtained in Example 3 (1.5 g) are dipped in 25 ml of acetone and one ml of triethylamine is added to the mixture. To the resultant mixture is further added dropwise 12 ml of a solution containing 1 g of succinic acid anhydride in acetone over 5 minutes and stirring is continued for 6 hours. After the reaction, the reaction product is separated by filtration, washed with water, then with 1N HCl, followed by washing with water, and then dried. Then, 1 g of the reaction product is charged into an Erlenmeyer's flask of 50 ml capacity and mixed with 3 ml of dioxane and 1 g of N-hydroxysuccinimide. While stirring the mixture under ice-cooling, 2 ml of dioxane containing 1 g of N,N'-dicyclohexylcarbodiimide dissolved therein is added dropwise thereto over about 10 minutes, and the mixture is left to stand at 10° C. overnight. After the reaction, the product is separated by filtration and washed by decantation using 20 times as much as its volume of dioxane. After removal of the insolubles, the product is further washed with dioxane and dried under reduced pressure. The reaction product having active esters (30 mg) is sufficiently swelled in 0.1M phosphate buffer (pH 7.5), followed by filtration, and put in 5 ml of an acylase solution (7.2 U/ml) produced from *Bacillus megaterium* B-400 (FERM-P 748). After the reaction is carried out while stirring the mixture at pH 7.5 for 4 hours in an ice-bath, the product is filtered and washed with 0.1M phosphate buffer (pH 7.5). Then, in 1M glycine/0.1M phosphate buffer (pH 7.5), stirring is continued at room temperature for 60 minutes to eliminate unaltered active ester groups. After filtration, the solid phase is washed with 0.5M sodium chloride/0.1M phosphate buffer (pH 7.5), and further with 0.1M phosphate buffer (pH 7.5), to give 840 mg (wet weight) of the immobilized enzyme having acylase bound to said particulate carrier (177.6 U/g).

EXAMPLE 20

Immobilization activity of enzymes on aminated porous and non-porous acrylonitrile polymer (PAN) fibers.

I. Preparation of carriers for immobilization

A. Materials (1) Porous PAN fibers

The fibers are provided by Asahi Kasei Kogyo Kabushiki Kaisha, Tokyo, Japan, made from acrylonitrilemethyl acrylate copolymer (acrylonitrile content=90% or more, average molecular weight=70,000–80,000, of 2–5 denier, whose pore diameter is 60–2000 Å, weight ratios of pores having 100–500 Å and 200–400 Å in diameter are about 65% and about 35%, respectively, and pore volume is 0.9 cm³/g.

(2) Non-porous polyacrylonitrile (PAN) fibers

The fibers are provided by Asahi Kasei Kogyo Kabushiki Kaisha above, whose pore volume is 0.065 cm³/g, of the same characters as above with respect to denier and polymer used.

B. Carriers for immobilization (1) Aminated porous PAN fibers of the present invention Dry porous PAN fibers (3 g) are suspended in anhydrous diethyl ether (150 ml) containing lithium aluminum hydride (1 g), and stirred for 30 min. at 38° C. with refluxing. The mixture is cooled to 5° C. and filtered through filter paper. The fibers on the filter are washed with ether to remove excess lithium aluminum hydride and stirred in diethyl ether (150 ml) with dropwise addition of 0.5N HCl (5 ml). The fibers are then collected by filtration, washed with 0.5N HCl (150 ml) and rinsed with water until the filtrate is no longer acidic to obtain aminated porous PAN fibers. Yield: about 9.7 g (wet) (=about 3 g in dry).

(2) Aminated nonporous PAN fibers

Aminated nonporous PAN fibers are obtained from dry nonporous PAN fibers using the same process as of 1) above. Yield: about 9.6 g (wet) (=about 3 g in dry).

(3) Content of primary amino group in fibers

Fibers thus obtained are cut into small pieces (80 mg) and suspended in 2 mM HCl (20 ml) with stirring for 60 min. at 20° C. Then the mixture is titrated with 2 mM NaOH. The content of primary amino group is calculated from the difference between titration values of the control and of the sample solution. The results are shown below.

| | |
|---|---|
| aminated porous PAN fibers | 230 μM/dry weight g |
| aminated nonporous PAN fibers | 20 μM/dry weight g |

II. Enzymes using for immobilization (1) Choline oxidase

Manufactured by Toyo Jozo Co., using *Arthrobacter globiformis* B-0577 (FERM-P 3518) (U.S. Pat. No. 4,135,980).

(2) Glucose oxidase

Manufactured by Boehringer Sohn A.G. (Mannheim).

(3) Lactate oxidase

Manufactured by Toyo Jozo Co.

(4) Phospholipase D

Manufactured by Toyo Jozo Co.

(5) Penicillin acylase

Manufactured by Toyo Jozo Co., using *Bacillus megaterium* B-400 (FERM-P 748).

*Bacillus megaterium* B-400 (FERM-P 748) is grown aerobically in culture medium consisting of 1% polypepton, 1% meat extract, 0.5% NaCl and 0.2% phenylacetic acid for 30 hr at 30° C. Then the cells are removed by centrifugation, and the supernatant is adjusted to pH 7 and mixed with Celite No. 560 (Johns Manvill Co., New York) (20 g/liter) with stirring for 2 hrs. The celite, which adsorbed penicillin acylase, is collected by filtration and washed with water. The enzyme is eluted by washing the celite with 24% ammonium sulfate in 0.1M phosphate buffer (pH 8.4). The eluate is dialyzed against 50 volumes of 50 mM phosphate buffer (pH 7.5). The dialyzate is concentrated to about one-third of its initial volume by ultrafiltration using polyacrylonitrile hollow fiber cartridges (Labo Module IL-100) having a nominal molecular weight cut-off of 6,000. The resulting concentrated solution has a specific activity of 28 units of penicillin acylase per unit of absorbance at 280 nm.

III. Method for the determination of the activity of enzymes

The same as described hereinbefore is used.

IV. Immobilization of enzyme using each carrier

A. Immobilization of choline oxidase (1) Immobilization using aminated porous PAN fibers of the present invention Three hundred miligrams of the aminated porous PAN fibers (wet) is put to 25 ml of 12.5%-glutaraldehyde/0.05M boric acid buffer solution (pH 8.5) and the mixture was agitated at 0° C. for 20 minutes for activation. Then the product is taken out by filtration and the residue is sufficiently washed with 0.05M boric acid buffer solution (pH 8.5). The product thus treated is put to 10 ml of choline oxidase solution (23 U/ml) and the mixture is allowed to react at 30° C. for 60 minutes under agitation. After the reaction is completed, the product is washed with 1M NaCl/0.1M phosphoric acid buffer solution (pH 7.5) and then with 0.1M phosphoric acid buffer solution (pH 7.0) to obtain about 300 mg of immobilized choline oxidase (38 U/g).

(2) Immobilization using aminated nonporous PAN fibers

Immobilized choline oxidase is obtained using aminated nonporous PAN fibers, in the same manner as in (1) above.

B. Immobilization of glucose oxidase (1) Immobilization using aminated porous PAN fibers of the present invention Immobilization of glucose oxidase is conducted according to the method similar to that mentioned in (A). That is, an activated PAN subjected to amination is put to 10 ml of a glucose oxidase solution (96 U/ml) and the mixture is allowed to react at 30° C. for 60 minutes under agitation. After the reaction is completed, the product is washed with a 1M-NaCl/0.1M-phosphoric acid buffer solution (pH 7.5) and then with a 0.1M-phosphoric acid buffer solution (pH 7.0) to obtain about 300 mg of immobilized glucose oxidase (73 U/g).

(2) Immobilization using aminated nonporous PAN fibers

Immobilized glucose oxidase is obtained using aminated nonporous PAN fibers in the same manner as (1) above.

C. Immobilization of lactate oxidase (1) Immobilization using aminated porous PAN fibers of the present invention Immobilization of lactate oxidase is conducted according to the method similar to that mentioned in (A). That is, an activated PAN subjected to amination is put to 10 ml of a lactate oxidase solution (26.6 U/ml) and the mixture is allowed to react at 30° C. for 60 minutes under agitation. After the reaction is completed, the product was washed with a 1M-NaCl/0.1M-phosphoric acid buffer solution (pH 7.5) and then with a 0.1M-phosphoric acid buffer solution (pH 7.0) to obtain about 300 mg of immobilized lactate oxidase (33 U/g).

(2) Immobilization using aminated nonporous PAN fibers

Immobilized glucose oxidase is obtained using aminated nonporous PAN fibers in the same manner as (1) above.

D. Immobilization of phospholipase D (1) Immobilization using aminated porous PAN fibers of present invention 600 mg (wet weight) of the aminated porous PAN fibers are put in 50 ml of a cold 12.5% glutaraldehyde/borate buffer (pH 8.5), followed by stirring at 0° C. for 20 minutes. The fibers are separated by filtration and then washed with a 0.1M phosphate buffer (pH 7.5). The fibers are mixed with 15 ml of a 0.1M phosphate buffer solution (pH 7.5) containing 40 U/ml of phospholipase D. The mixture is stirred at 30° C. for 60 minutes. The product is separated by filtration and washed with a 0.5M sodium chloride/0.1M phosphate buffer (pH 7.5) to give immobilized, phospholipase D bound to said porous carrier (phospholipase D activity 68 U/g).

(2) Immobilization using aminated nonporous PAN fibers

Immobilized phospholipase D is obtained using aminated nonporous PAN fibers in the same manner as (1) above.

E. Immobilization of Penicillin acylase using aminated PAN fibers (1) Immobilization using aminated porous PAN fibers of present invention Aminated porous PAN fibers (3 g) are mixed with 12.5% (w/v) glutaraldehyde in 0.1M sodium borate buffer (pH 8.5) (190 ml) with stirring for 20 min. at 0° C. The mixture is filtered through a glass filter, and the fibers activated with glutaraldehyde are washed on the filter with 0.1M phosphate buffer (pH 7.5) (10 l) and immediately suspended in a penicillin acylase solution (65 units/ml) (250 ml). The suspension is stirred for 16 hr. at 5° C., and the resulting fibers, to which the acylase is linked with glutaraldehyde, are recovered by filtration and washed with 0.5M NaCl in 0.1M phosphate buffer (pH 7.5) (500 ml).

(2) Immobilization using aminated nonporous PAN fibers

Immobilized penicillin acylase linked with glutaraldehyde using aminated nonporous PAN fibers is prepared in the same manner as (1) above.

V. Activities of enzymes determined

| Enzyme | Specific activity (U/g carrier) Carrier | |
|---|---|---|
| | aminated porous PAN fibers of the present invention | aminated nonporous PAN fibers |
| Choline oxidase | 38 | 2 |
| Glucose oxidase | 73 | 4 |
| Lactate oxidase | 33 | 2 |
| Phospholipase D | 68 | 5 |
| Penicillin acylase | 2800 | 80 |

From the above, the present aminated porous PAN fibers can immobilize a remarkably larger amount of choline oxidase, glucose oxidase, lactate oxidase, phospholipase D and penicillin acylase than aminated nonporous PAN fibers.

EXAMPLE 21

Relationship between the pore diameter and the pore volume of polyacrylonitrile (PAN) fibers.

A. Materials (1) Porous PAN fibers

Lot No. 109, No. 102 and No. 115 of the fibers are provided by Asahi Kasei Kogyo Kabushiki Kaisha, Tokyo, Japan, made from acrylonitrile-methyl acrylate copolymer (acrylonitrile content =90% average molecular weight=70,000-80,000, of 2-5 denier).

(2) Non-porous PAN fibers

Lot No. 105 and No. 113 of the fibers are provided by Asahi Kasei Kogyo Kabushiki Kaisha above, of the same characters as above with respect to denier and polymer used.

B. Measurement of pore diameter and pore volume of PAN fibers above

Relationship between the pore diameter and the pore volume of the porous and non-porous PAN fibers that are prepared at different conditions of spinning are measured by mercury porosimetry.

Figure 1:
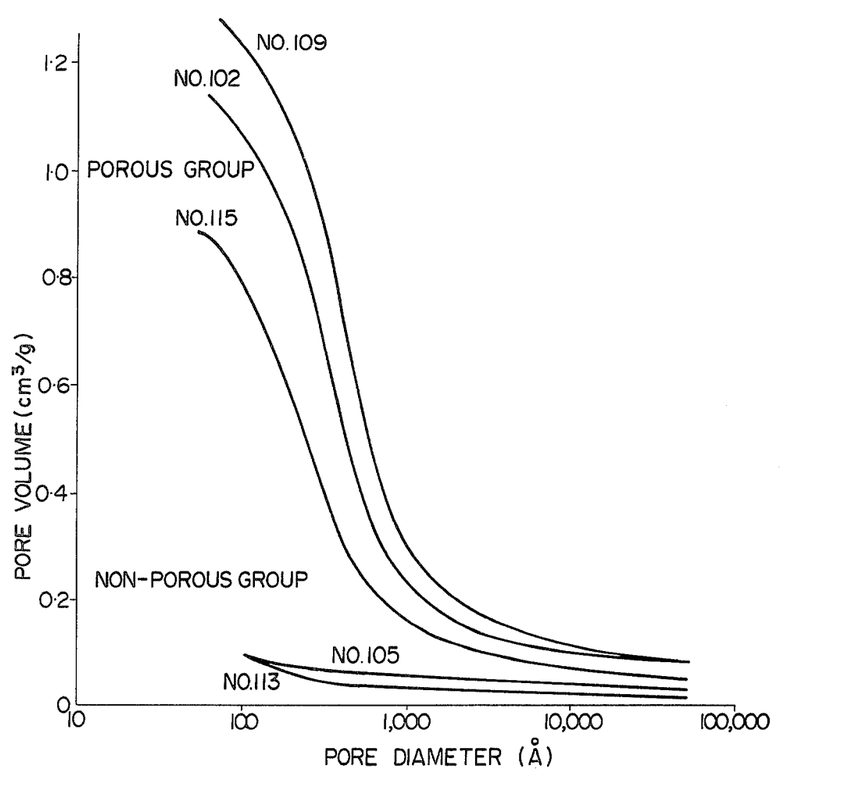

FIG. 1 shows the result measured, in which the pore diameters are 50-2000 Å, preferably 100-1000 Å and the pore volumes are as follows:

| fibers | | per volumes | |
|---|---|---|---|
| Porous group | Lot No. 109 | 1.28 | cm³/g |
| | Lot No. 102 | 1.14 | |
| | Lot No. 115 | 0.90 | |
| Non-porous group | Lot No. 105 | 0.065 | cm³/g |
| | Lot No. 113 | 0.065 | |

C. Penicillin acylase immobilization on PAN fibers

Aminated PAN fibers are prepared from the fibers above according to example 20, I, B and immobilized penicillin acylase is prepared according to example 20, IV (E). Activities of the enzyme measured are as follows:

| fibers | | penicillin acylase activity | |
|---|---|---|---|
| porous group | Lot No. 109 | 2,800 | units/g |
| | Lot No. 102 | 3,200 | |
| | Lot No. 115 | 2,400 | |
| non-porous group | Lot No. 105 | 80 | units/g |
| | Lot No. 113 | 90 | |

The above substantiates that pore diameter of the present porous PAN fibers suitable for having enzyme immobilized is 50-2000 Å, preferably 100-1000 Å and that the present porous PAN fibers can strongly immobilize enzyme while non-porous PAN fibers cannot.

What we claim is:

1. A process for producing an acrylonitrile polymer containing amino groups and having a porous structure containing micro-pores with an average size of from 50 to 2000 Å and pore volume of not less than 0.2 cm³/g, which comprises reducing an acrylonitrile polymer having said porous structure in an inert non-solvent for said polymer with lithium aluminum hydride.

2. A process according to claim 1, wherein the acrylonitrile polymer is in the form of a fiber, a particle, a membrane or a hollow filament.

3. A process according to claim 1, wherein the acrylonitrile polymer is a polymer of an acrylonitrile monomer of a copolymer of said monomer with a comonomer having ethylenically unsaturated double bond.

4. A process according to claim 3, wherein the acrylonitrile monomer is acrylonitrile, methacrylonitrile, α-chloroacrylonitrile of cinnamnitrile.

5. A process according to claim 3, wherein the comonomer is a styrene monomer, an acrylic acid ester monomer, a conjugated diene, a halogenated olefin, a vinyl ether monomer, a vinyl ketone monomer, a vinyl ester monomer, an amide vinyl monomer, a basic monomer or a polyfunctional monomer.

6. A process according to claim 3, wherein the acrylonitrile polymer has a porous structure with micropores having sizes distributed in the range form about 100 to 1,000 Å and is constituted of polyacrylonitrile containing 90% or more of acrylonitrile shaped in the form of a fiber, a particle, a membrane or a hollow filament.

7. A process according to claim 3, wherein the acrylonitrile polymer is a copolymer consisting of acrylonitrile, divinyl benzene and vinyl ethyl benzene shaped in the form of a fiber, a particle, a membrane or a hollow filament.

8. A process according to claim 1, wherein the non-solvent is an organic solvent which does not dissolve an acrylonitrile polymer and an acrylonitrile polymer containing amino groups.

9. A process according to claim 8, wherein the organic solvent is diethyl ether, dioxane or tetrahydrofuran.

10. A process according to claim 1, wherein the reduction is effected to an extent which does not make the acrylonitrile polymer containing amino groups substantially soluble in water.

11. A process according to claim 10, wherein the reduction is carried out for 10 minutes to 30 hours.

12. A process according to claim 1, wherein the acrylonitrile polymer contains amino groups in an amount which does not make the polymer substantially soluble in water.

13. A process according to claim 12, wherein the acrylonitrile polymer contains 20 μM to 1000 μM of amino groups per gram of the polymer.

14. A process according to claim 1, wherein the acrylonitrile polymer has a porous structure with micropores having sizes distributed in the range from about 100 to 1,000 Å.

* * * * *